United States Patent [19]
Lin et al.

[11] Patent Number: 5,851,485
[45] Date of Patent: Dec. 22, 1998

[54] PROCESS FOR STERILIZATION WITH LIQUID STERILANT USING CONTROLLED PUMPDOWN RATE

[75] Inventors: Szu-Min Lin, Laguna Hills; Paul Taylor Jacobs, Trabuco Canyon, both of Calif.

[73] Assignee: Johnson & Johnson Medical, Inc., New Brunswick, N.J.

[21] Appl. No.: 891,866

[22] Filed: Jul. 9, 1997

Related U.S. Application Data

[60] Provisional application No. 60/033,692 Dec. 20, 1996.
[51] Int. Cl.$^6$ .................................. A61L 2/00; A61L 2/16
[52] U.S. Cl. .................................. 422/33; 422/28; 422/27; 422/292
[58] Field of Search .................................. 422/33, 28, 27, 422/292

[56] References Cited

U.S. PATENT DOCUMENTS

| | | | |
|---|---|---|---|
| 4,169,123 | 9/1979 | Moore et al. | 422/29 |
| 4,169,124 | 9/1979 | Forstrom et al. | 422/23 |
| 4,643,876 | 2/1987 | Jacobs et al. | 422/23 |
| 4,943,414 | 7/1990 | Jacobs et al. | 422/28 |
| 4,952,370 | 8/1990 | Cummings et al. | 422/28 |
| 5,492,672 | 2/1996 | Childers et al. | 422/28 |
| 5,656,238 | 8/1997 | Spencer et al. | 422/23 |

Primary Examiner—Robert J. Warden
Assistant Examiner—Fariborz Moazzam
Attorney, Agent, or Firm—Knobbe, Martens, Olson, & Bear, LLP

[57] ABSTRACT

A method for sterilizing a device, includes the following steps: contacting the device with liquid sterilant outside or inside a sterilization chamber at a first pressure, placing the device in the chamber before or after the contacting step, and decreasing the pressure of the chamber to a second pressure below the vapor pressure of the liquid sterilant. At least the decrease in pressure below about the vapor pressure of the liquid sterilant occurs at a pumpdown rate of less than 0.8 liters per second, calculated based on the time required to evacuate the chamber from atmospheric pressure to 20 torr when the chamber is empty and dry.

56 Claims, 6 Drawing Sheets

PROCESS FOR STERILIZATION WITH LIQUID STERILANT USING CONTROLLED PUMPDOWN RATE

RELATED APPLICATION

The present application claims the benefit of the filing date under 35 U.S.C. § 119(e) of Provisional Application Ser. No. 60/033,692, filed Dec. 20, 1996.

FIELD OF THE INVENTION

The present invention relates to a process for sterilization of medical instruments using a liquid sterilant. More particularly, the invention relates to a process in which sterilization is achieved by vaporizing hydrogen peroxide using a controlled pump down rate.

BACKGROUND OF THE INVENTION

Medical instruments have traditionally been sterilized using either heat, such as is provided by steam, or a chemical, such as formaldehyde or ethylene oxide in the gas or vapor state. Each of these methods has its drawbacks. Many medical devices such as fiberoptic devices, endoscopes, power tools, etc., are sensitive to heat, moisture or both. Formaldehyde and ethylene oxide are both toxic gases that pose a potential hazard to healthcare workers. Problems with ethylene oxide are particularly severe, because its use requires long aeration times to remove the gas from articles that have been sterilized. This makes the sterilization time undesirably long.

Sterilization using liquid hydrogen peroxide solution has been found to require high concentrations of sterilant, extended exposure time and/or elevated temperatures. However, sterilization using hydrogen peroxide vapor has been shown to have some advantages over other chemical sterilization processes (see, e.g., U.S. Pat. (Nos. 4,169,123 and 4,169,124). The combination of hydrogen peroxide with a plasma provides certain additional advantages, as disclosed in U.S. Pat. No. 4,643,876. The sterilization of articles containing diffusion-restricted areas, such as long narrow lumens, presents a special challenge. Methods that use hydrogen peroxide vapor that has been generated from an aqueous solution of hydrogen peroxide have certain disadvantages. One disadvantage is that because water has a higher vapor pressure than hydrogen peroxide, it will vaporize faster. Another disadvantage is that because of its lower molecular weight, water will diffuse faster than hydrogen peroxide in the vapor state. Because of these physical properties, when an aqueous solution of hydrogen peroxide is vaporized in the area surrounding the items to be sterilized, the water reaches the items first and in higher concentration. The water vapor therefore becomes a barrier to the penetration of hydrogen peroxide vapor into diffusion-restricted areas, such as small crevices and long narrow lumens. This problem cannot be addressed by removing water from the aqueous solution and using more concentrated hydrogen peroxide because, among other reasons, hydrogen peroxide solutions greater than 65% by weight can be hazardous due to their oxidizing potential.

U.S. Pat. No. 4,952,370 discloses a sterilization process in which aqueous hydrogen peroxide vapor is first condensed on the article to be sterilized, followed by application of a vacuum to the sterilization chamber to evaporate the water and hydrogen peroxide from the article. This method is suitable for surface sterilization, but not for sterilization of diffusion-restricted areas such as long narrow lumens because it depends on the diffusion of hydrogen peroxide vapor into the lumen to effect sterilization.

U.S. Pat. No. 4,943,414 discloses a process in which a vessel containing a small amount of a vaporizable liquid sterilant solution is attached to a lumen, and the sterilant vaporizes and flows directly into the lumen of the article as the pressure is reduced during the sterilization cycle. This system has the advantage that the water and hydrogen peroxide vapor are pulled through the lumen by the existing pressure differential, increasing the sterilization rate for lumens, but has the disadvantage that the vessel needs to be attached to each lumen to be sterilized. In addition, water is vaporized faster and precedes the hydrogen peroxide vapor into the lumen.

In U.S. Pat. No. 5,492,672, there is disclosed a process for sterilizing narrow lumens. This process uses a multicomponent sterilant vapor and requires successive alternating periods of flow of sterilant vapor and discontinuance of such flow. A complex apparatus is used to accomplish the method. Because flow through of vapor is used, closed end lumens are not readily sterilized in the process.

Thus, there remains a need for a simple and effective method of vapor sterilization of articles having areas where diffusion of these vapors is restricted, such as long narrow lumens.

SUMMARY OF THE INVENTION

One embodiment of the present invention is a method for sterilizing a device, comprising the steps of contacting the device with liquid sterilant outside or inside a sterilization chamber at a first pressure; placing the device in the chamber before or after the contacting step; and decreasing the pressure of the chamber to a second pressure below the vapor pressure of the liquid sterilant in which at least a portion of the decrease in pressure below about the vapor pressure of the liquid sterilant occurs at a pumpdown rate of less than 0.8 liters per second, calculated based on the time required to evacuate the chamber from atmospheric pressure to 20 torr when the chamber is empty and dry, i.e. when the chamber has neither articles to be sterilized nor a visible quantity of liquid within it. According to one aspect of this preferred embodiment, at least the decrease in pressure below about two times the vapor pressure of the liquid sterilant occurs at a pumpdown rate of less than 0.8 liters per second. According to another aspect of this preferred embodiment, the decrease in pressure below about four times the vapor pressure of the liquid sterilant occurs at a pumpdown rate of less than 0.8 liters per second. Preferably, the pumpdown rate is 0.6 liters per second or less; more preferably, 0.4 liters per second or less; and most preferably, 0.2 liters per second or less. Advantageously, the first pressure is atmospheric pressure. Preferably, the liquid sterilant is hydrogen peroxide. In another aspect, the device is a medical instrument having a lumen.

The present invention also provides a method for sterilizing a device comprising the steps of (a) contacting the device with liquid sterilant outside or inside a sterilization chamber at a first pressure; (b) placing the device in the chamber before or after the contacting step; (c) pumping down the chamber to a second pressure which is lower than the first pressure at a first rate; and (d) pumping down the chamber to a third pressure which is lower than the second pressure, wherein at least a portion of the pumping down to the third pressure is at a second rate which is slower than the first rate. The pumpdown rate either above and/or below the second pressure can be constant or variable. In certain embodiments, the pumpdown rate either above and/or below the second pressure is reduced in stepwise fashion. Preferably, the second pressure is greater than or equal to about the vapor pressure of the liquid sterilant; more preferably, the second pressure is greater than or equal to about two times the vapor pressure of the liquid sterilant; most preferably, the second pressure is greater than or equal to about four times the vapor pressure of the liquid sterilant. Advantageously, the pumpdown rate in step (d) is 0.8 liters/sec or less; more advantageously 0.6 liters/sec or less; even more advantageously 0.4 liters/sec or less; and most advantageously 0.2 liters/sec or less, calculated based on the time required to evacuate the chamber from atmospheric pressure to 20 torr under empty and dry conditions. Preferably, the liquid sterilant is hydrogen peroxide. In another aspect of this embodiment, the device is a medical instrument having a lumen. Preferably, the pumping down of step (c) reduces the pressure to less than about three times, more preferably to less than about two times, the vapor pressure of the liquid sterilant.

Another aspect of the present invention is a method for sterilizing an article in a sterilization chamber. This method includes contacting the article with liquid sterilant either inside or outside of the sterilization chamber, placing the device in the chamber either before or after the contacting step, and reducing the pressure of the chamber while regulating the pumpdown rate so as to control the evaporation rate of sterilant in said chamber. In any of the methods described above, the contacting step may comprise application of liquid or condensed vapor. These methods described above may additionally comprise further evacuating the chamber to remove residual sterilant. Further, these methods described above may additionally comprise exposing the device to plasma to remove residual sterilant or enhance sterilization efficacy. The contacting step in these methods can be either by direct or indirect contacting. As stated hereinbelow, indirect contacting involves introducing sterilant into the chamber without directly contacting the article to be sterilized.

Another embodiment of the invention is an apparatus for sterilizing an article, comprising: a chamber containing a liquid sterilant; a first valve and a second valve fluidly connected to the chamber, wherein each of the valves is adapted to regulate the pressure of the chamber, and wherein the first valve regulates the pressure of the chamber at a faster pumpdown rate than the second valve; and a pump fluidly connected to the valves for reducing the pressure in the chamber. Preferably, the second valve is smaller than the first valve. In one aspect of this preferred embodiment, the first valve is connected to a first vacuum line and the second valve is connected to a second vacuum line, wherein the second vacuum line is smaller than the first vacuum line. The valves may be configured in parallel or serially configured.

The present invention also provides an apparatus for sterilizing an article comprising: a chamber containing a liquid sterilant; two or more pumps fluidly connected to the chamber for reducing the pressure in the chamber; and two or more valves, each of the valves being fluidly connected to at least one of the pumps and to the chamber, wherein each of the valves is adapted to independently regulate the pressure of the chamber.

Sill another embodiment of the invention is an apparatus for sterilizing an article comprising: a chamber containing a liquid sterilant; a first pump and a second pump for reducing the pressure in the chamber, each of the pumps being fluidly connected to the chamber, wherein the first pump provides a faster pump down rate than the second pump; and a valve fluidly connected to each of the pumps and to the chamber, wherein the valve is adapted to regulate the pressure of said chamber.

DETAILED DESCRIPTION OF THE PREFERRED EMBODIMENTS

Sterilizing the inside of lumened devices has always posed a challenge to sterilization systems. Copending U.S. application Ser. No. 08/628,965, the entire contents of which are hereby incorporated by reference, discloses a method of hydrogen peroxide vapor sterilization of diffusion-restricted environments, such as long narrow lumens, at pressures less than the vapor pressure of hydrogen peroxide by pretreating the article to be sterilized with a dilute solution of hydrogen peroxide prior to exposure to a vacuum.

In the copending application referred to above, it is demonstrated that the inside of long narrow lumens can be effectively sterilized by taking advantage of the diffusion-restricted environments within the lumens. We have now discovered that conditions similar to those created in diffusion-restricted environments can be created through controlling the evacuation rate of the chamber in which articles to be sterilized are placed. These conditions allow for the effective sterilization of both diffusion-restricted and non-diffusion-restricted spaces. Thus, both the inside and outside of articles can be sterilized without the need for special containers or equipment.

In the present invention, inherent problems associated with prior art sterilization systems are overcome in a sterilization process in which the pump down rate is controlled. In this process, a sterilization chamber is evacuated slowly to create some of the benefits achieved when diffusion of sterilant occurs from inside to outside of a diffusion restricted environment which is being sterilized. This process simulates a diffusion restricted environment because water, which has a higher vapor pressure than hydrogen peroxide, vaporizes first and is rapidly removed from the system, resulting in concentration of hydrogen peroxide.

Figure 1:
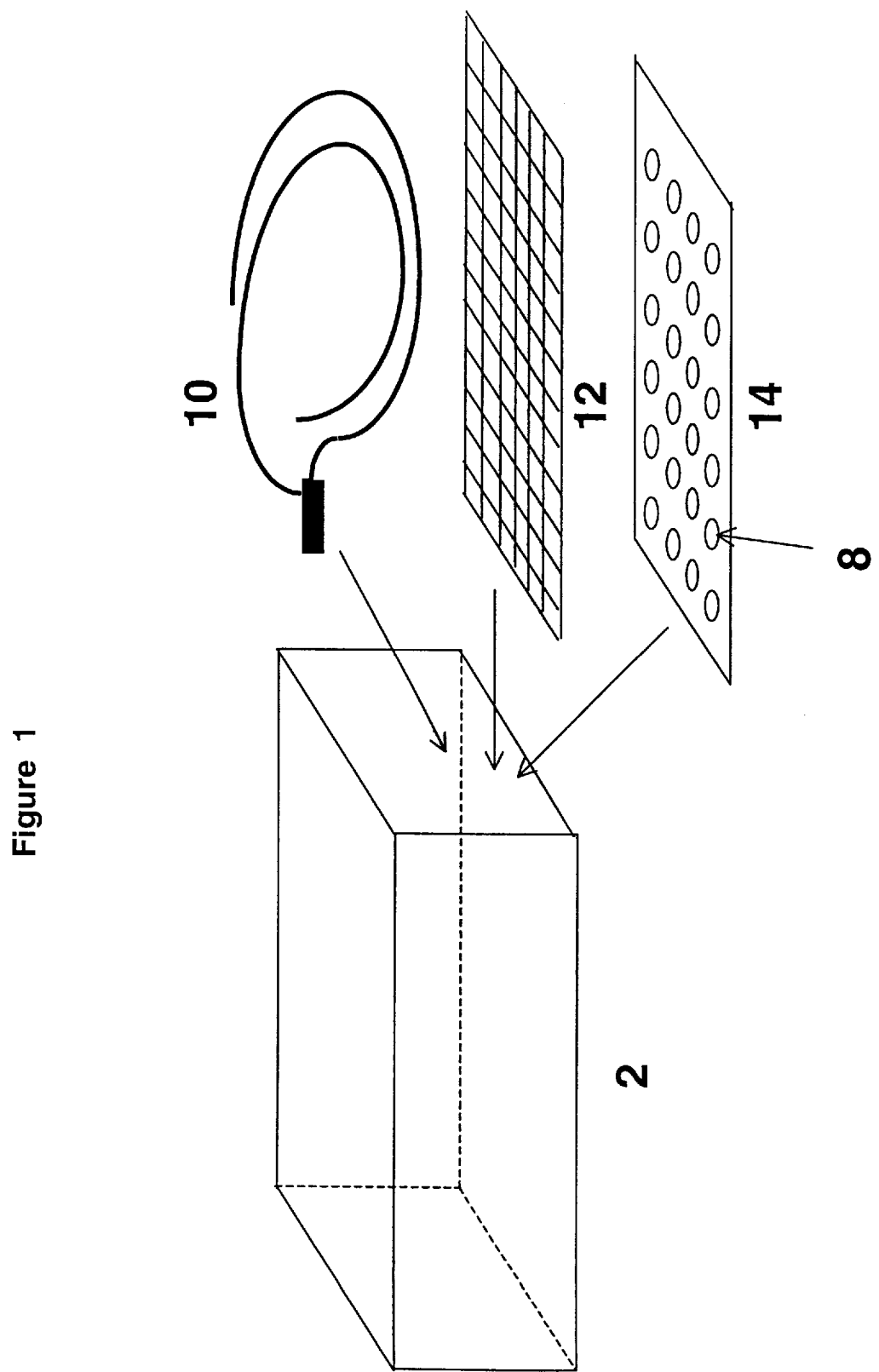
FIG. 1 is a schematic diagram of a chamber and accessories suitable for use in the hydrogen peroxide sterilization process of the invention.
Figure 2:
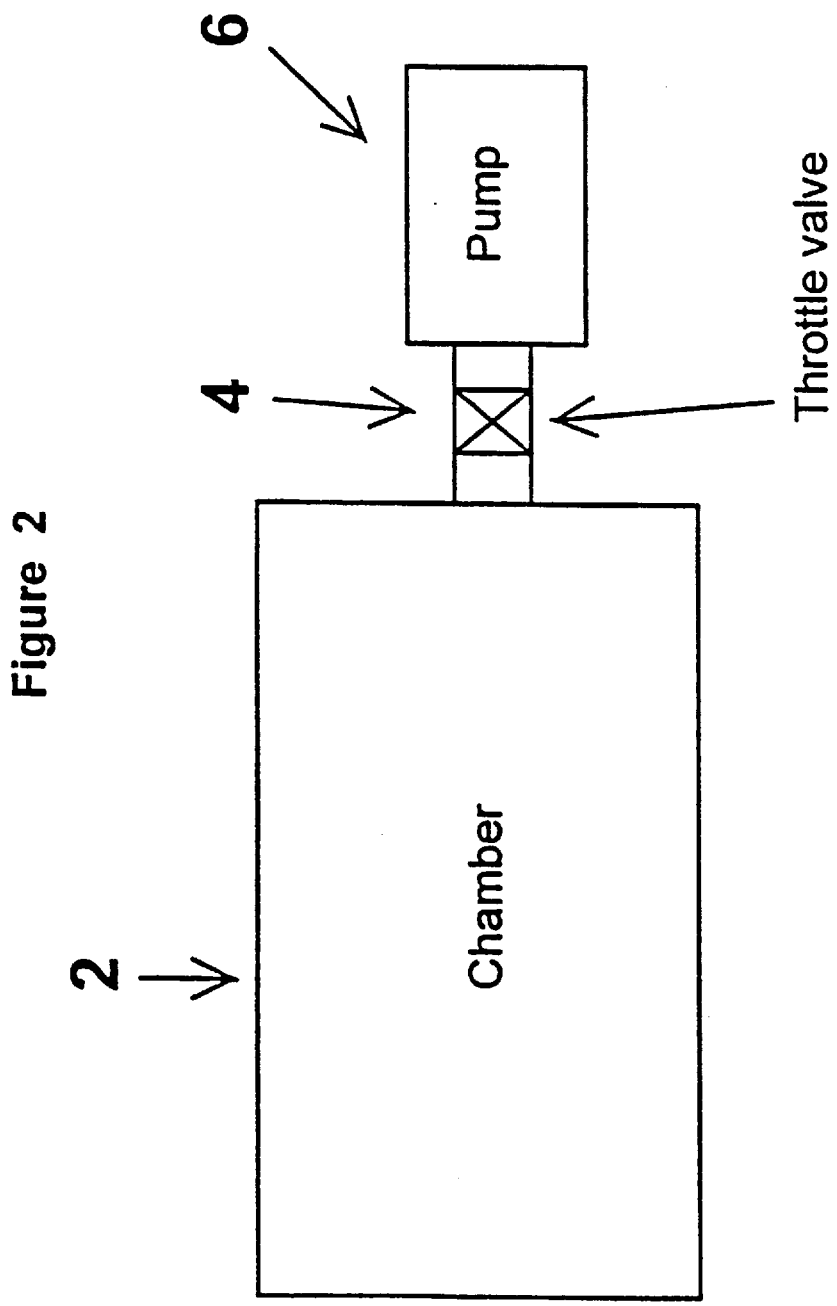
FIG. 2 is a schematic diagram of a chamber, pump and throttle valve for use in the hydrogen peroxide sterilization process of the invention.

An apparatus useful in the process of the present invention is shown schematically in FIGS. 1 and 2 and comprises a chamber 2, a throttle valve 4 and a pump 6. In FIG. 2, the chamber 2 is attached to the pump 6 by the throttle valve 4. The valve 4 can be controlled either automatically or manually to maintain the pressure. Manual control can be used to achieve a slower pumpdown rate. In the automatic mode of operation, the throttle valve 4 opens based on the pressure in the chamber via a pressure transducer and valve controller. Such valves are commercially available from, for example, MKS (Andover, Md.). In this process a dilute, aqueous solution of hydrogen peroxide is placed in wells 8 as shown in FIG. 1. The aqueous solution of hydrogen peroxide can also be placed within the lumen of long narrow objects to be sterilized. As the pressure in the sterilization chamber 2 is reduced, the hydrogen peroxide vaporizes and contacts the surface to be sterilized (i.e., colonoscope 10 in FIG. 1) which is placed on metal grid 12 which rests on tray 14. In a preferred embodiment, the tray can be configured with a plurality of wells designed to retain a known volume of liquid sterilant. In one embodiment, the volume of sterilization chamber 2 is about 18.5 liters and its dimensions are about 22" (55.9 cm)×4.25" (10.8 cm)×12" (30.5 cm).

Figure 3:
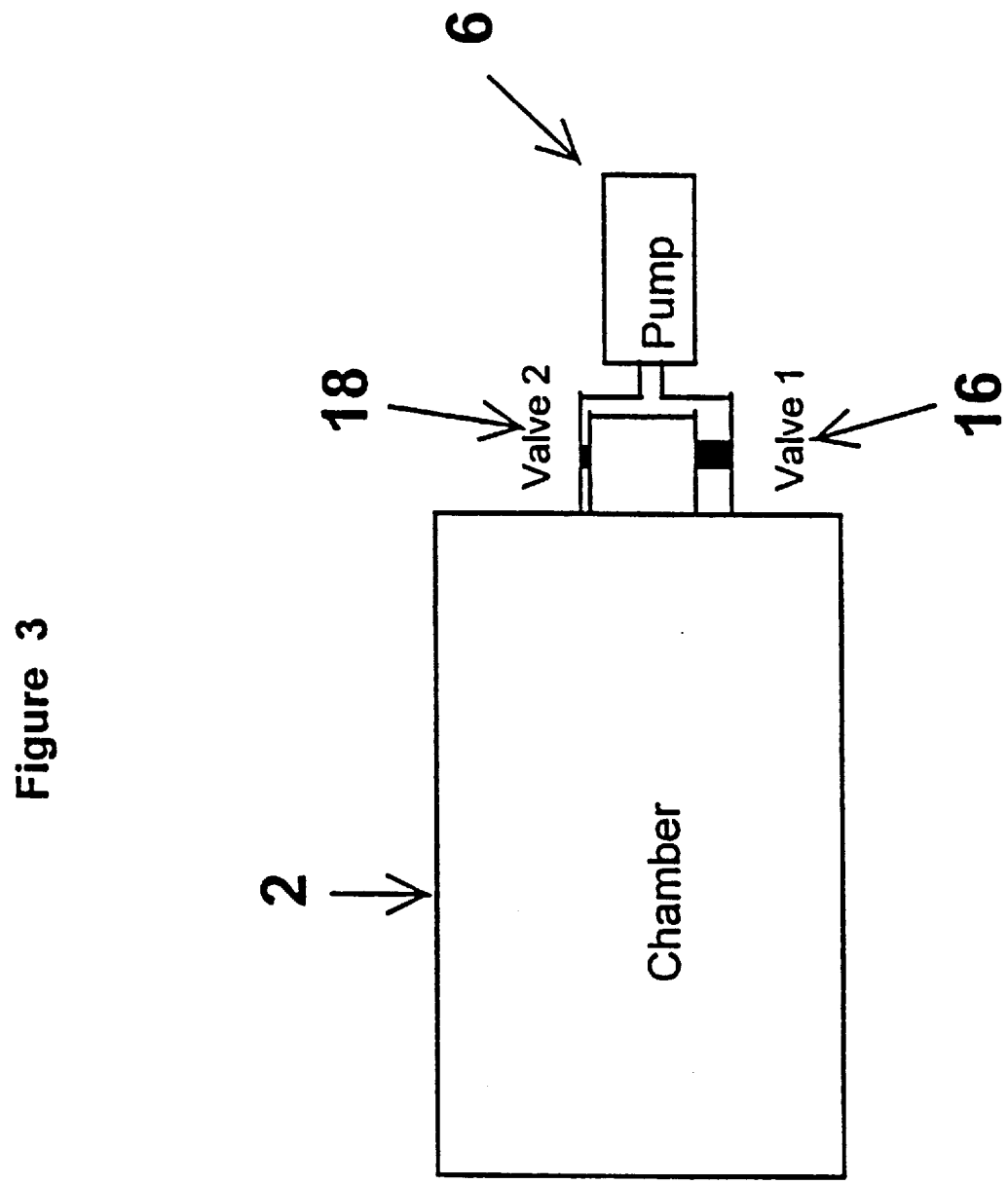
FIG. 3 is a schematic diagram of a system with one pump and two valves, one valve having a larger pump vacuum line for quicker pumpdown and one having a smaller vacuum line for slower pumpdown.

FIG. 3 illustrates a parallel two-valve arrangement for use in the sterilization process of the invention. In this embodiment, the chamber 2 is in fluid communication with the pump 6 via valves 16 and 18. Valve 16 mediates the initial rapid evacuation, the first step of the two step evacuation process. Valve 18 mediates slow evacuation, the second step of the process, which ensures maximal contact of the article to be sterilized with the vaporized aqueous hydrogen peroxide. The pumpdown rate can be controlled by the pumping speed and/or the percent opening of the valve. Either valve can be used to maintain the pressure.

Figure 4:
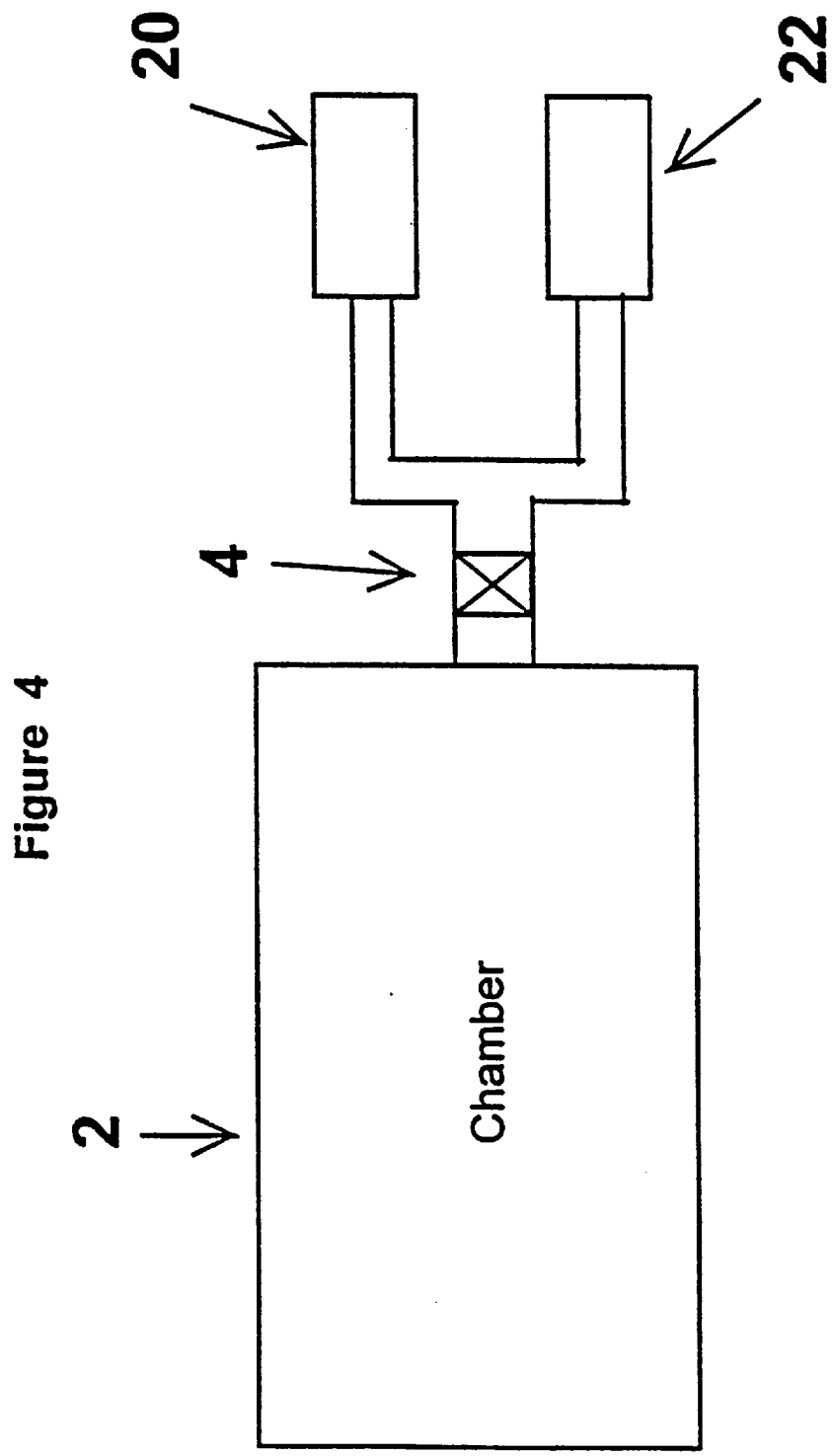
FIG. 4 is a schematic diagram of a single valve sterilization system having two pumps, one for slower pumpdown and one for quicker pumpdown.
Figure 5:
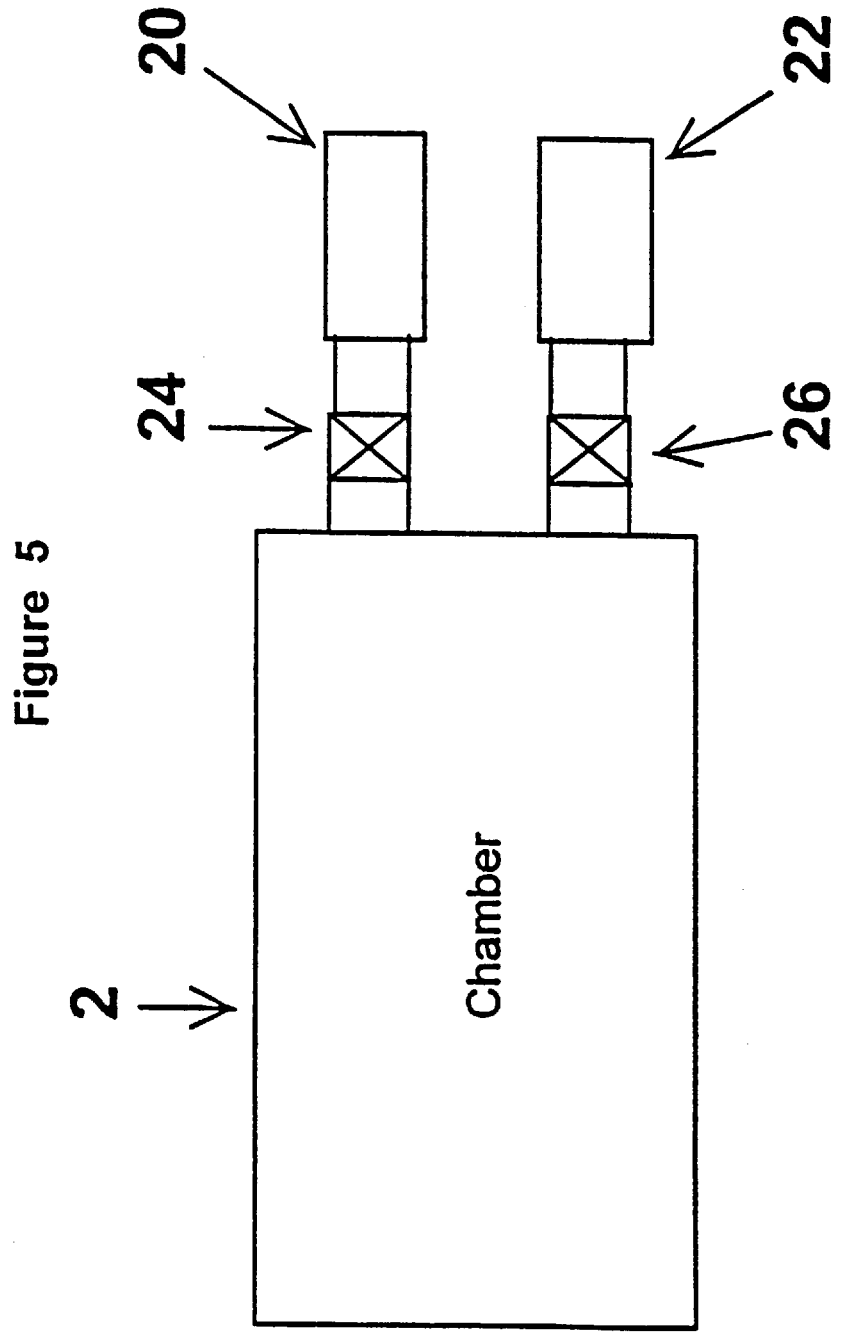
FIG. 5 is a schematic diagram of a system with two pumps and two valves, one pump for slower pumpdown and one for quicker pumpdown.
Figure 6:
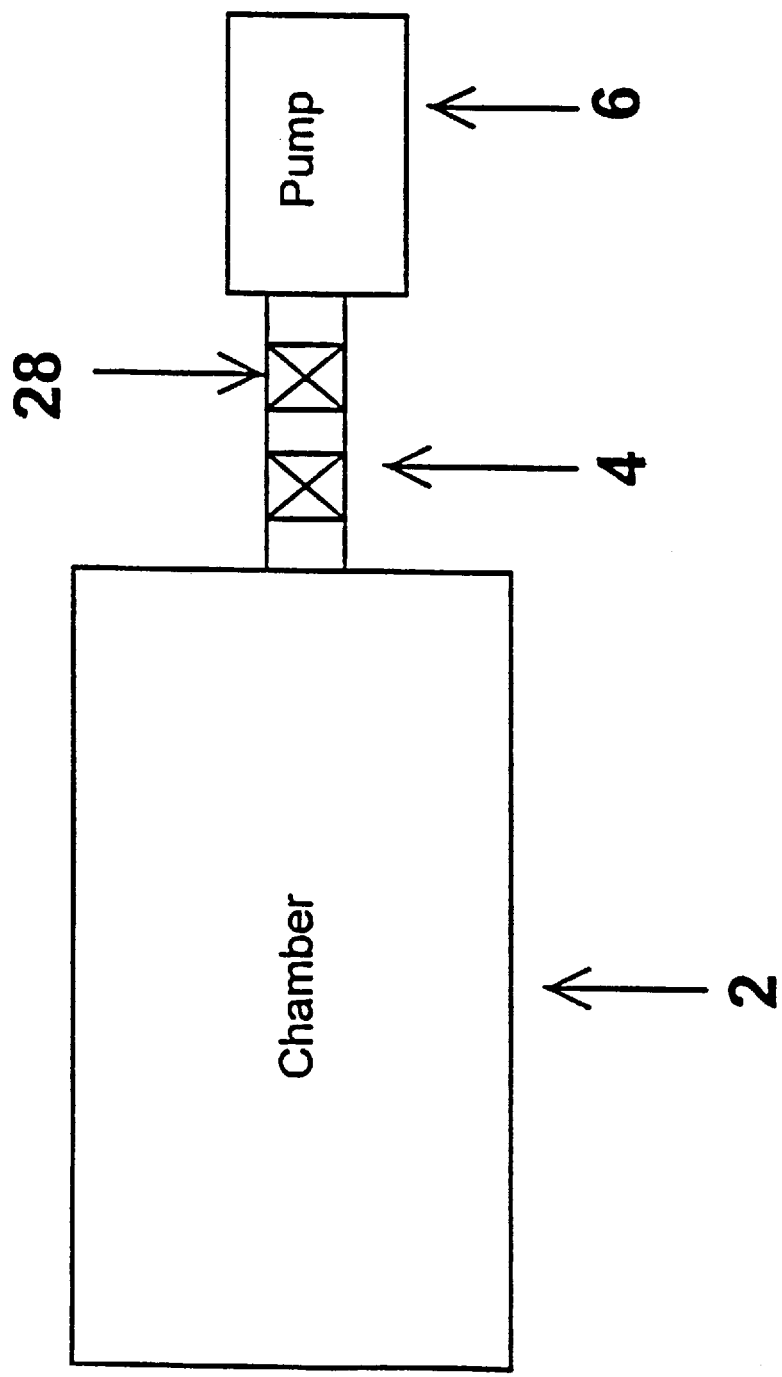
FIG. 6 is a schematic diagram of a system with one pump and two valves, a throttle valve and a manual valve, for more controlled regulation of the pumpdown rate.

FIG. 4 illustrates a sterilization apparatus having two pumps 20 and 22, and one valve 4. Pump 20 allows quicker pumpdown of the chamber 2, while pump 22 allows slower pumpdown. FIG. 5 illustrates an alternate configuration having two valves 24 and 26 in fluid communication with the pumps 20 and 22, respectively. FIG. 6 illustrates another configuration having a throttle valve 4 and a manual valve 28 serially arranged in fluid communication with the pump 6. The manual valve 28 allows more precise control of pumpdown rate of the chamber 2.

Regardless of which configuration is used, hydrogen peroxide can be introduced into the chamber as a liquid. In a preferred embodiment, hydrogen peroxide is introduced as a vapor and the chamber parameters are changed so that the vapor condenses as a liquid on the surface of interior of an article to be sterilized. Such changes include increasing the pressure.

The aqueous solutions of hydrogen peroxide can be relatively dilute, e.g. as low as 1–6% peroxide by weight, since sterilization is not achieved through contact with the hydrogen peroxide solution, but rather is achieved at low temperatures (preferably 15°–80° C., more preferably 20°–60° C., still more preferably 40°–55° C.) and in short periods of time (preferably less than one hour, and more preferably less than one-half hour) upon exposure to hydrogen peroxide under vacuum. The method of the present invention is particularly effective with articles having inaccessible or hard-to-reach places. Such articles include long, narrow lumens, hinges and other articles having spaces where diffusion of vapors is restricted. Although hydrogen peroxide is used in the examples described herein, the use of other liquid sterilants which have vapor pressures lower than the vapor pressure of the solvent in which they are provided are also contemplated. Such sterilants include, for example, aqueous peracetic acid solution and aqueous glutaraldehyde solution.

Contacting of the article to be sterilized with sterilant can be accomplished either directly or indirectly. Direct contacting includes methods such as static soaking, flow through, aerosol spray, condensation of a vapor. Any other methods involving physically contacting the articles to be sterilized with sterilant would be considered direct contacting. Indirect contacting includes those methods in which sterilant is introduced into the chamber, but not directly on or in the articles to be sterilized.

At the end of the process, deep vacuum can be used to remove residual sterilant. A plasma can also be used to remove residual sterilant and to enhance sterilization efficacy.

The term "pumpdown rate" as used herein is based on the time required to evacuate the chamber from atmospheric pressure (760 torr) to 20 torr when the chamber is empty and dry, i.e. when the chamber has neither articles to be sterilized nor a visible quantity of liquid within it. The "pumpdown rate" is calculated as the volume of the chamber being evacuated divided by the time which would be required to evacuate the chamber to 20 torr using a particular configuration. This particular configuration includes the configuration of the pump, the chamber and any material between the pump and the chamber, such as valves or tubing. Thus, as used herein, the "pumpdown rate" is a constant for any particular configuration even though the actual rate of pumping may naturally vary through the pumping cycle when using that particular configuration.

The pumps shown schematically in the figures can be any commercially available pump. Two preferred pumps are from Leybold Vacuum Products, Inc. (Export, Pa.) (Model D16A, pump rate=400 liters/min) and KNF Neuberger, Inc. (Trenton, N.J., Model N740, pump rate=45 liters/min). The Leybold pump can reach a pressure of less than 0.1 torr and the KNF pump can reach a pressure of less than 10 torr. To compare the effect of pumpdown rate on efficacy, the chamber was evacuated to either 20 torr or 25 torr. The parameters were as follows: temperature of chamber=45° C.; 2.3×10$^6$ *Bacillus stearothermophilus* (Bst) per SS blade; blades on insertion tube of Olympus CF10 colonoscope; 48 drops×50 μl/drop 6% H$_2$O$_2$. The results are shown in Table 1 and are expressed as a ratio of the number of inoculated blades which remain contaminated after treatment over the number of inoculated blades tested.

TABLE 1

| Pressure | Pump Used | Mode of Throttle Valve | Time Required to Execute | Exposure Time | Total Time Under Vacuum | Sterility Results |
|---|---|---|---|---|---|---|
| 25 torr | KNF | Automatic | 5 min 5 sec | 5 min | 10 min 5 sec | 0/2 |
|  | Leybold | Automatic | 35 sec | 5 min | 5 min 35 sec | 2/2 |
|  |  |  |  | 10 min | 10 min 35 sec | 2/2 |
| 20 torr | KNF | Automatic | 5 min 50 sec | 5 min | 10 min 50 sec | 0/2 |
|  | Leybold | Automatic | 35 sec | 5 min | 5 min 35 sec | 2/2 |
|  |  |  |  | 10 min | 10 min 35 sec | 2/2 |

As shown in Table 1, the efficacy results were better with the KNF pump with the same exposure time under vacuum. The KNF pump took about five more minutes to evacuate the chamber than the Leybold pump.

Because the lowest pressure which can be reached with the KNF pump is about 10 torr, the Leybold pump with manual controlled throttle valve at 20% opening was used to compare the pumpdown rate at a pressure lower than 10 torr. The throttle valve was controlled at 20% opening during the evacuation and set to automatic mode when the set pressure was reached. The reaction parameters were as follows: T=45° C.; $2.3 \times 10^6$ Bst per blade; location of blades= uncovered petri dish; 48 drops×50 μl/drop 6% $H_2O_2$. The results are shown in Table 2.

TABLE 3

| Pump | % opening of throttle valve | Time required to evacuate chamber | Pumpdown rate (liters/second) |
|---|---|---|---|
| KNF | 100% | 195 sec. | 0.09 |
| Leybold | 100% | 15 sec. | 1.23 |
|  | 20% | 93 sec. | 0.20 |

The effect of pumpdown rate on the efficacy of the liquid/vapor sterilization process was then investigated at various pumpdown rates. The pumpdown rates were deter-

TABLE 2

| Pressure | Pump Used | Mode of Throttle Valve | Time Required to Evacuate | Exposure Time | Total Time Under Vacuum | Sterility Results |
|---|---|---|---|---|---|---|
| 5 torr | Leybold | Automatic | 40 sec | 5 min | 5 min 40 sec | 2/2 |
|  |  |  |  | 10 min | 10 min 40 sec | 2/2 |
|  |  |  |  | 30 min | 30 min 40 sec | 2/2 |
|  |  |  |  | 60 min | 60 min 40 sec | 1/2 |
|  |  |  |  | 120 min | 120 min 40 sec | 0/2 |
|  |  | Manual (20% opening) | 5 min 15 sec | 5 min | 10 min 15 sec | 0/2 |
| 1 torr | Leybold | Automatic | 50 sec | 5 min | 5 min 50 sec | 2/2 |
|  |  |  |  | 10 min | 10 min 50 sec | 2/2 |
|  |  |  |  | 30 min | 30 min 50 sec | 2/2 |
|  |  |  |  | 60 min | 60 min 50 sec | 2/2 |
|  |  |  |  | 120 min | 120 min 50 sec | 1/2 |
|  |  |  |  | 180 min | 180 min 50 sec | 0/2 |
|  |  | Manual at 20% opening | 24 min 30 sec | 10 min | 34 min 30 sec | 0/2 |

As seen from the data set forth in Table 2, when the throttle valve was controlled automatically, only 40 and 50 seconds were required to reduce the pressure to 5 and 1 torr, respectively. Under these conditions, 2–3 hours were required to effect complete sterilization. In contrast, complete sterilization was achieved in 5–10 minutes when the valve was set at a 20% opening. Although it takes longer to pump down the chamber using these parameters, the overall time is less.

The results from Tables 1 and 2 indicate that the efficacy of sterilization can be controlled by the pumpdown rate. While not wishing to be bound by any particular mode of action, it is believed that when the chamber was evacuated slowly, the gradual evacuation of the chamber simulates what would occur when sterilant diffuses from inside of a diffusion-restricted area to the outside thereof. It is believed that the water solvent vaporizes first and is removed from the system, while the peroxide vaporizes more slowly and persists in contact with the article. Thus, the peroxide is concentrated within the system to achieve more rapid sterilization. When the chamber is evacuated rapidly, no such concentration of peroxide occurs, leaving a lower concentration of peroxide vapor to sterilize the article so it necessarily takes longer to achieve complete sterilization.

The pumpdown rate of the Leybold and KNF pumps under various conditions from atmospheric pressure to 20 torr is summarized in Table 3. The chamber used was an 18.5 liter chamber which was dry and empty without sterilant. The apparatus used was that shown in FIG. 2.

mined based on the time required to evacuate an 18.5 liter chamber which was dry and empty without sterilant from 1 atmosphere to 20 torr. The apparatus used to determine efficacy was that shown in FIG. 2 for 93 and 15 second pumpdown time points (i.e. 0.20 liters/second and 1.23 liters/second pumpdown rates). The apparatus used for the 23, 30 and 60 second pumpdown time points (i.e. 0.80 liters/second, 0.62 liters/second and 0.31 liters/second pumpdown rates) is that shown in FIG. 6. The pumpdown rate was controlled by setting the manual valve 28 at various openings. The temperature of the chamber was 45° C. The stainless steel (SS) blades were inoculated with 2.3× $10^6$ Bacillus stearothermophilus (Bst) per blade for the results taken at pumpdown rates of 0.20 and 1.23 liters/sec, and were inoculated with $1.9 \times 10^6$ Bst per blade for the results taken at 0.31, 0.62 and 0.80 liters/sec. The blades were in an uncovered petri dish, and the chamber carried a load of an Olympus CF10 colonoscope. 48 drops of 6% liquid hydrogen peroxide at 50 μl/drop were placed inside the chamber. The results are summarized in Table 4.

TABLE 4

| Time to evacuate chamber to 20 torr | Pump down rate | Efficacy of peroxide with Bst/SS blade at 5 torr pressure | | | | | | | |
|---|---|---|---|---|---|---|---|---|---|
| | | 5 min | 10 min | 20 min | 30 min | 40 min | 50 min | 60 min | 120 min |
| 93 seconds | 0.20 | 0/2 | — | — | — | — | — | — | — |
| 60 seconds | 0.31 | 2/2 | 0/2 | 0/2 | — | — | — | — | — |
| 30 seconds | 0.62 | 2/2 | 2/2 | 2/2 | 0/2 | 0/2 | — | — | — |
| 23 seconds | 0.80 | 2/2 | 2/2 | 2/2 | 1/2 | 1/2 | 1/2 | 1/2 | — |
| 15 seconds | 1.23 | 2/2 | 2/2 | — | 2/2 | — | — | 1/2 | 0/2 |

The results show that at pumpdown rates of less than 0.8 liters/second, sterilization is significantly enhanced over the sterilization efficacy achieved with a pumpdown rate of 1.23 liters/second. The sterilization efficacy using reduced pumpdown rates will depend upon the load in the chamber, the peroxide concentration, the volume of peroxide, the temperature and the volume of the chamber. All of these factors will affect the vapor concentration of peroxide in the chamber during the sterilization process. In a preferred embodiment, these factors will be adjusted to produce a vapor concentration of at least 0.05 mg/l of hydrogen peroxide, more preferably at least 0.1 mg/l and still more preferably 0.2 mg/l or more. There is no upper limit other than the saturation limits of the system as to the amount of peroxide which can be present in the vapor phase while still achieving efficacy.

For certain substrates being sterilized, such as nylon or polyurethane, excess hydrogen peroxide in the system may leave a residual which is difficult to remove. In order to avoid an excess residual, the vapor concentration of hydrogen peroxide is preferably kept below 30 mg/l, more preferably less than 20 mg/l, and more preferably still less than 15 mg/l. If higher vapor concentrations of hydrogen peroxide are desired, excess residual can be removed using a gas plasma. When using substrates such as stainless steel, polyethylene or polypropylene, which do not retain a residual, there is no reason to limit the amount of peroxide which can be present in the vapor phase in the system during sterilization.

Using the particular conditions described above, the desired vapor concentrations of peroxide during sterilization can be achieved with a pumpdown rate less than 0.8 liters/sec for evacuating an empty dry chamber from atmospheric pressure to 20 torr. More preferably, the pumpdown rate is 0.6 liters/sec or less, still more preferably 0.4 liters/sec or less, and even more preferably 0.2 liters/sec or less. These pumpdown rates can be effective for chambers as small as one liter or as large as 2000 liters. However, more preferably, these pumpdown rates are used for chambers in the range 2-1000 l, more preferably still in the range 5-200 l, and even more preferably in the range 10-100 l.

Because the majority of the sterilant does not vaporize until the pressure approaches four times the vapor pressure of the liquid sterilant, the system can be evacuated quickly at the beginning and then pumped down more slowly when the pressure approaches the vapor pressure of the sterilant. Thus, in a preferred embodiment of the invention, the gradual reduction of pressure is done in two steps to shorten the time required for sterilization. In the first step, the pressure is quickly reduced from atmospheric pressure to a pressure above that at which concentration of the sterilant occurs. Thus, in a preferred embodiment, the first step brings the chamber down to about the vapor pressure or more, more preferably about two times the vapor pressure or more, and still more preferably about four times the vapor pressure or more. The first step pumpdown rate is greater than 0.8, 0.6, 0.4 or 0.2 liters/sec, while the second step pumpdown rate is about 0.8, 0.6, 0.4 or 0.2 liters/sec or less. These pumpdown rates are based on the time required to evacuate a dry empty chamber from 760 torr to 20 torr.

The first step pumpdown rate from atmospheric pressure to the pressure above that at which concentration of the sterilant occurs (the second pressure) may be constant, variable or reduced in a stepwise fashion. Similarly, the second step pumpdown rate from this second pressure to a third pressure may be constant, variable or reduced in a stepwise fashion.

The pressure at which this first step is performed will depend on the vapor pressure of the sterilant under the desired sterilization conditions. Typically, the pressure is about four times the vapor pressure of the sterilant. More preferably, the pressure is about three times the vapor pressure of the sterilant. Most preferably, the vapor pressure is about twice the vapor pressure of the sterilant. Thus, in a typical example, the initial, rapid pump down can reduce pressure to the 200–400 torr pressure range. In the second step, the pressure is gradually reduced from 200–400 torr to the preferred pressure range for sterilization. The optimal pressure for the second step is within the range 0.1–80 torr, more preferably 1–50 torr, still more preferably 1–20 torr.

It should be noted that the present invention is not limited to only those embodiments described in the Detailed Description. Any embodiment which retains the spirit of the present invention should be considered to be within its scope. However, the invention is only limited by the scope of the following claims.

What is claimed is:

1. A method for sterilizing a device in a sterilization chamber, comprising the steps of:
   contacting said device with liquid sterilant at a first pressure, said liquid sterilant having a vapor pressure;
   placing said device in said chamber; and
   decreasing the pressure of said chamber to a second pressure below the vapor pressure of the liquid sterilant in which at least a portion of the decreasing in pressure below about the vapor pressure of the liquid sterilant occurs at a pumpdown rate of less than 0.8 liters per second, calculated based on the time required to evacuate the chamber from atmospheric pressure to 20 torr when the chamber is empty and dry.

2. The method of claim 1, wherein the contacting step is conducted outside said sterilization chamber.

3. The method of claim 1, wherein the contacting step is conducted after the placing step.

4. The method of claim 1, wherein at least the decrease in pressure below about two times the vapor pressure of the liquid sterilant occurs at a pumpdown rate of less than 0.8 liters per second.

5. The method of claim 1, wherein at least the decrease in pressure below about four times the vapor pressure of the liquid sterilant occurs at a pumpdown rate of less than 0.8 liters per second.

6. The method of claim 1, wherein said pumpdown rate is 0.6 liters per second or less.

7. The method of claim 4, wherein said pumpdown rate is 0.4 liters per second or less.

8. The method of claim 5, wherein said pumpdown rate is 0.2 liters per second or less.

9. The method of claim 1, wherein said first pressure is atmospheric pressure.

10. The method of claim 1, wherein said liquid sterilant is hydrogen peroxide.

11. The method of claim 1, wherein said device is a medical instrument having a lumen.

12. The method of claim 1, wherein said contacting step comprises application of liquid or condensed vapor.

13. The method of claim 1, additionally comprising further evacuating the chamber to remove residual sterilant.

14. The method of claim 1, additionally comprising exposing said device to plasma to remove residual sterilant or enhance sterilization efficacy.

15. The method of claim 1, wherein the contacting step comprises introducing sterilant into the chamber without directly contacting the article to be sterilized.

16. The method of claim 1, wherein the volume of said chamber is in the range from about one liter to about 2000 liters.

17. The method of claim 1, wherein the volume of said chamber is in the range from about 10 liters to about 100 liters.

18. A method for sterilizing a device in a sterilization chamber, comprising the steps of:
(a) contacting said device with liquid sterilant at a first pressure;
(b) placing said device in said chamber;
(c) pumping down said chamber to a second pressure which is lower than the first pressure at a first rate; and
(d) pumping down said chamber to a third pressure which is lower than the second pressure, wherein at least a portion of the pumping down to said third pressure is at a second rate which is slower than said first rate.

19. The method of claim 18, wherein the contacting step is conducted outside said sterilization chamber.

20. The method of claim 18, wherein the contacting step is conducted after the placing step.

21. The method of claim 18, wherein the pumpdown rate above said second pressure is constant.

22. The method of claim 18, wherein the pumpdown rate above said second pressure is variable.

23. The method of claim 18, wherein the pumpdown rate above said second pressure is reduced in stepwise fashion.

24. The method of claim 18, wherein the pumpdown rate below said second pressure is constant.

25. The method of claim 18, wherein the pumpdown rate below said second pressure is variable.

26. The method of claim 18, wherein the pumpdown rate below said second pressure is reduced in stepwise fashion.

27. The method of claim 18, wherein the second pressure is greater than or equal to about the vapor pressure of the liquid sterilant.

28. The method of claim 18, wherein the second pressure is greater than or equal to about two times the vapor pressure of the liquid sterilant.

29. The method of claim 18, wherein the second pressure is greater than or equal to about four times the vapor pressure of the liquid sterilant.

30. The method of claim 18, wherein the pumpdown rate in step (d) is 0.8 liters/sec or less, calculated based on the time required to evacuate the chamber from atmospheric pressure to 20 torr when the chamber is empty and dry.

31. The method of claim 18, wherein the pumpdown rate in step (d) is 0.6 liters/sec or less, calculated based on the time required to evacuate the chamber from atmospheric pressure to 20 torr when the chamber is empty and dry.

32. The method of claim 18, wherein the pumpdown rate in step (d) is 0.4 liters/sec or less, calculated based on the time required to evacuate the chamber from atmospheric pressure to 20 torr when the chamber is empty and dry.

33. The method of claim 18, wherein the pumpdown rate in step (d) is 0.2 liters/sec or less, calculated based on the time required to evacuate the chamber from atmospheric pressure to 20 torr when the chamber is empty and dry.

34. The method of claim 18, wherein said liquid sterilant is hydrogen peroxide.

35. The method of claim 18, wherein said device is a medical instrument having a lumen.

36. The method of claim 18, wherein the pumping down of step (c) reduces the pressure to less than about three times the vapor pressure of the liquid sterilant.

37. The method of claim 18, wherein the pumping down of step (c) reduces the pressure to less than about two times the vapor pressure of the liquid sterilant.

38. The method of claim 18, wherein said contacting step comprises application of liquid or condensed vapor.

39. The method of claim 18, additionally comprising further evacuating the chamber to remove residual sterilant.

40. The method of claim 18, additionally comprising exposing said device to plasma to remove residual sterilant or enhance sterilization efficacy.

41. The method of claim 18, wherein the contacting step comprises introducing sterilant into the chamber without directly contacting the article to be sterilized.

42. A method for sterilizing an article in a sterilization chamber, comprising the steps of:
contacting said article with liquid sterilant solution comprising hydrogen peroxide and water;
placing said article in said chamber; and
reducing the pressure of said chamber at a rate selected to control removal of the water and hydrogen peroxide so as to concentrate the hydrogen peroxide remaining in said chamber.

43. The method of claim 42, wherein the contacting step is conducted outside said chamber.

44. The method of claim 42, wherein the placing step is conducted before the contacting step.

45. The method of claim 42, wherein said contacting step comprises application of liquid or condensed vapor.

46. The method of claim 42, additionally comprising further evacuating the chamber to remove residual sterilant.

47. The method of claim 42, additionally comprising exposing said device to plasma to remove residual sterilant or enhance sterilization efficacy.

48. The method of claim 42, wherein the contacting step comprises introducing sterilant into the chamber without directly contacting the article to be sterilized.

49. The method of claim 42, wherein the reducing step produces a vapor concentration of hydrogen peroxide of at least 0.05 mg/l in the sterilization chamber.

50. The method of claim 49, wherein the reducing step produces a vapor concentration of hydrogen peroxide in the range from about 0.2 mg/l to about 30 mg/l in the sterilization chamber.

51. An apparatus for sterilizing an article comprising:

a chamber having liquid sterilant therein;

a first valve and a second valve fluidly connected to said chamber, wherein each of said valves is adapted to regulate the pressure of said chamber, and wherein the first valve is configured to regulate the pressure of the chamber at a faster pumpdown rate than the second valve is configured; and a pump fluidly connected to said valves for reducing the pressure in said chamber.

52. The apparatus of claim 51, wherein said second valve is smaller than said first valve.

53. The apparatus of claim 51, wherein said first valve is connected to a first vacuum line and said second valve is connected to a second vacuum line, wherein said second vacuum line is smaller than said first vacuum line.

54. The apparatus of claim 51, wherein said valves are configured in parallel.

55. The apparatus of claim 51, wherein said valves are serially configured.

56. An apparatus for sterilizing an article comprising:

a chamber having liquid sterilant therein;

a first pump and a second pump for reducing the pressure in said chamber, each of said pumps being fluidly connected to said chamber, wherein said first pump provides a faster pump down rate than the second pump; and a valve fluidly connected to each of said pumps and to said chamber, wherein said valve is adapted to regulate the pressure of said chamber.

* * * * *